United States Patent [19]

Schwab et al.

[11] 4,218,332

[45] Aug. 19, 1980

[54] TETRASULFIDE EXTREME PRESSURE LUBRICANT ADDITIVES

[75] Inventors: Arthur W. Schwab; Lyle E. Gast, both of Peoria, Ill.; Harold E. Kenney, Jenkintown, Pa.

[73] Assignee: The United States of America as represented by the Secretary of Agriculture, Washington, D.C.

[21] Appl. No.: 22,128

[22] Filed: Mar. 20, 1979

Related U.S. Application Data

[63] Continuation of Ser. No. 833,883, Sep. 16, 1977, abandoned.

[51] Int. Cl.$^2$ ............... C10M 1/38; C10M 1/26; C10M 1/24; C10M 3/32
[52] U.S. Cl. ............... 252/48.6; 260/399; 549/13; 549/79; 568/21; 568/26
[58] Field of Search ............... 252/48.6; 260/608, 399; 549/13, 79

[56] References Cited

U.S. PATENT DOCUMENTS

| | | | |
|---|---|---|---|
| 2,307,307 | 1/1943 | Shoemaker | 252/48.6 |
| 2,382,700 | 8/1945 | Eby | 252/45 |
| 2,468,739 | 5/1949 | Eaton et al. | 260/609 B |
| 2,479,996 | 8/1949 | Bell et al. | 260/609 B |
| 2,649,416 | 8/1953 | Richter et al. | 252/48.6 |
| 2,790,775 | 4/1957 | Hughes et al. | 252/45 |
| 3,022,351 | 2/1962 | Mihm et al. | 260/608 |
| 3,238,179 | 3/1966 | Heuck et al. | 260/45.95 R |
| 3,991,089 | 11/1976 | Schwab et al. | 252/48.6 |
| 4,000,078 | 12/1976 | Baldwin et al. | 297/167 |

FOREIGN PATENT DOCUMENTS 714497  9/1954  United Kingdom ............... 252/48.6

OTHER PUBLICATIONS

Schwab et al., JAOCS 52, (7): 236–239, 1975.
Schwab et al., JAOCS 53, (12): 762–766, 1975.
Koenig et al., J. Arg. Chem. 23, 1525–1530, 1958.
Guryanova et al., CA 57: 5833g.

*Primary Examiner*—Delbert E. Gantz
*Assistant Examiner*—Irving Vaughn
*Attorney, Agent, or Firm*—M. Howard Silverstein; David G. McConnell; Curtis P. Ribando

[57] ABSTRACT

A novel class of compounds has been prepared comprising the tetrasulfides of $C_{18}$ hydrocarbons, $C_{18}$ fatty acids, and $C_{18}$ fatty and alkyl and triglyceride esters. These tetrasulfides are useful as extreme pressure lubricant additives and show potential as replacements for sulfurized sperm whale oil.

8 Claims, No Drawings

TETRASULFIDE EXTREME PRESSURE LUBRICANT ADDITIVES

This is a continuation of application Ser. No. 833,883, filed Sept. 16, 1977, abandoned.

BACKGROUND OF THE INVENTION

1. Field of the Invention

This invention relates to extreme pressure (EP) additives which are added to lubricants to prevent destructive metal-to-metal contact in lubrication of moving surfaces at high pressures and/or temperatures. EP additives are useful in certain gear elements in automotive vehicles and various industrial machines where high pressure can cause a film of lubricant to rupture.

2. Description of the Prior Art

Sulfurized sperm whale oil has been an effective EP agent, but its use has been curtailed by the Endangered Species Act. In search for a substitute, efforts have been made to prepare wax esters chemically similar to those that constitute 70-75% of sperm whale oil. Perlstein et al., JAOCS 51: 35 (1974), describe some synthetic wax ester preparations from fatty compounds, but these were found to be of limited effectiveness.

Sulfurized synthetic lubricant additives have included compounds such as sulfurized polyisobutylene, thienyl derivatives, trithiones, diphenyl disulfide, and di-n-butyl disulfide. Lubricant compositions comprising hydrogen sulfide adducts of olefins are taught in U.S. Pat. No. 2,382,700, 2,468,739, 2,479,996, 3,991,089, and 4,000,078. Polysulfide lubricant additives have also been synthesized, such as the dimethylbenzyl tetrasulfide cutting oil agent taught by Hughes et al. in U.S. Pat. No. 2,790,775. However, none of these compounds have exhibited sufficient extreme pressure values comparable to sulfurized sperm oil.

SUMMARY OF THE INVENTION

A class of compounds has now been discovered which unexpectedly has EP properties equal to or superior to those of sulfurized sperm whale oil. These compounds include the tetrasulfide derivatives of $C_{18}$ hydrocarbons, $C_{18}$ fatty acids, and $C_{18}$ fatty acid alkyl and triglyceride esters.

It is an object of the invention to chemically prepare these novel tetrasulfide compounds.

Another object of the invention is to provide at least one species of tetrasulfides which is derivatized from readily available petroleum fractions, and others from renewable vegetable sources.

It is also an object of the invention to provide EP lubricant additives which are effective substitutes for sulfurized sperm whale oil.

DETAILED DESCRIPTION OF THE INVENTION

The general structure of the tetrasulfide derivatives included within the scope of this invention is as follows:

$$R^1-S-S-S-S-R^2$$

wherein $R^1$ and $R^2$ are each independently selected from the following substituent groups:

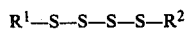  I

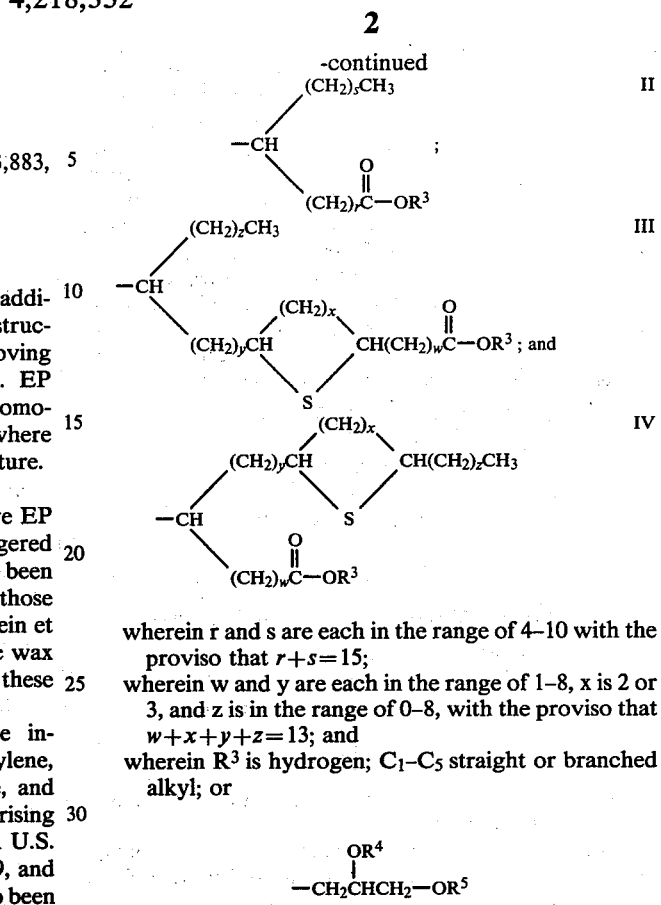

wherein r and s are each in the range of 4-10 with the proviso that $r+s=15$;

wherein w and y are each in the range of 1-8, x is 2 or 3, and z is in the range of 0-8, with the proviso that $w+x+y+z=13$; and wherein $R^3$ is hydrogen; $C_1-C_5$ straight or branched alkyl; or

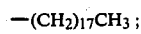

wherein $R^4$ and $R^5$ are each independently selected from the acyl radicals of $C_{16}-C_{18}$ saturated and unsaturated fatty acids, and from the acyl radicals of the mercapto, thiolan and thiane derivatives of $C_{18}$ unsaturated fatty acids.

The instant tetrasulfides corresponding to the above structural formulas can be prepared in either a two-step process from $C_{18}$ mono- and triunsaturated olefins, or else directly from the mercapto derivatives of these olefins. Exemplary olefinic precursors include 1-octadecene, oleic acid, linolenic acid, and oleic and linolenic lower alkyl and triglyceride esters. Of course, it is understood that isomers of oleic and linolenic acids and their alkyl and triglyceride esters could also be used. Preferred from an economic standpoint are the oleic acid-containing and linolenic acid-containing vegetable oils or their methyl ester transesterification products. Oleic acid-containing vegetable oils are defined herein to mean those glyceride oils containing oleic acid as one of the major components of the glyceride structure, such as soybean oil, sunflower oil, olive oil, and cottonseed oil. Likewise, linolenic acid-containing materials include oils comprised predominantly of linolenic acid, such as linseed oil and perilla oil.

The olefinic materials may be converted to their mercaptan derivatives by any procedure as known in the art. Preferred is the boron trifluoride-catalyzed, nucleophilic addition of $H_2S$ at $-70°$ C. as taught in Schwab et al., JAOCS 52(7): 236-239 (1975); Schwab et al., JAOCS 53(12): 762-766 (1976); and U.S. Pat. No. 3,991,089. Free radical addition of $H_2S$ discussed in Schwab et al. (1976), supra, and free radical addition of thiolacetic acid followed by hydrolysis as taught by Koenig et al., J. Org. Chem. 23: 1525-1530 (October 1958), are alternative methods of mercaptan preparation, though generally not as effective as the nucleophilic addition. As described in the Schwab et al. references, supra, H$_2$S addition to di- and triunsaturated nonconjugatable compounds is preferential to intramolecular cyclization over the addition of a second hydrogen sulfide. Five-membered thiolans predominate as the cyclic structures with some six-membered thianes also being formed. Once cyclization occurs in a triene, the remaining double bond is available for mercapto formation. It is to be understood that the method of mercaptan preparation does not constitute novelty of the invention, and that other procedures may be employed provided that the resultant mercaptan conform to one of the following structural formulas:

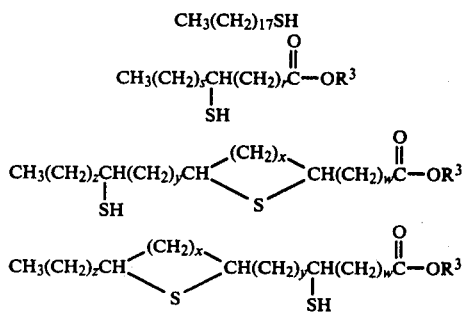

wherein r, s, w, x, y, z, and R$^3$ have the same values as set forth previously.

The novel tetrasulfides are prepared by crosslinking the two molecules of mercaptan with sulfur monochloride as follows:

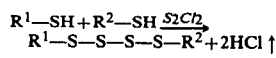

where R$^1$ and R$^2$ are selected from the structures defined above and may be the same or different from one another. The reaction is effected by adding dropwise the sulfur monochloride to the stirred mercaptan in a solvent. Since the reaction is exothermic, it is usually necessary to cool the reaction vessel. After addition of the final drop, the solution is refluxed for 1–2 hours at temperatures of about 65°–80° C. to drive off hydrogen chloride. Any common organic solvent such as hexane, petroleum ether, heptane, cyclohexane, etc. would be suitable. After the reaction, the solvent is stripped off under reduced pressure or by another conventional procedure as appropriate. The tetrasulfides are recovered and may be purified as desired.

The novel EP additives can be incorporated into any lubricant base oil as known in the art. Particularly suitable are straight petroleum mineral oils, and preferably those which have been refined by well-known processes such as alkali-refining, solvent extraction, hydrogenation, etc. It is preferred that the base oil be a solvent for the additive, though auxiliary solvent agents may be used if necessary. Lubricants treated with the additives of the present invention may be used as crankcase oils, transmission oils, cutting oils, extruding oils, rolling oils, drawing oils, continuous steel casting lubricants, and for other industrial uses demanding lubrication of contacting surfaces at high pressures.

For most uses, it is desirable to employ about 1–10% by weight tetrasulfide in the base oil. At the preferred 5% addition level, the EP value of white mineral oil is surprisingly increased from 130 kg. up to as high as about 580 kg. The same quantity of sulfurized sperm oil containing 10% sulfur imparts to the mineral oil an EP value of only 220 kg.

The following examples are intended only to further illustrate the invention and are not intended to limit the scope of the invention which is defined by the claims.

EXAMPLE 1

Preparation of n-octadecyl tetrasulfide

Into a 1-liter round-bottom flask equipped with a "Teflon"-coated magnetic stirrer was weighed 14.3 g. (0.05 mole) n-octadecyl mercaptan. 300 ml. hexane (redistilled Skelly B b.p. 67°–70° C.) were added and stirred until all the mercaptan was dissolved. In a 100-ml. beaker, 3.37 g. sulfur monochloride (0.025 mole) were dissolved in 80 ml. hexane. The S$_2$Cl$_2$ solution was transferred to a dropping funnel and added dropwise to the stirred mercaptan solution. After all of the sulfur monochloride had been added, the reaction mixture was refluxed for 1 hour to drive off the hydrogen chloride. The resultant clear and slightly yellow solution was admixed with 380 ml. of dry acetone and refrigerated at 5° C. Crystals of n-octadecyl tetrasulfide separated from the solution and were filtered and vacuum dried. 15.1 g. of dried crystals were recovered having a melting point of 44°–45° C.

EXAMPLE 2

Preparation of bis[octadecanoic acid 9(10)-yl]tetrasulfide

Into a 100-ml. round-bottom flask equipped with a magnetic stirrer was weighed 12.4419 g. 9(10)-mercaptostearic acid. 50 ml. hexane (redissolved Skelly B b.p. 67°–70° C.) were added and stirred until all the sample was in solution. In a 50-ml. beaker, 2.4371 g. sulfur monochloride were dissolved in 20 ml. hexane. The S$_2$Cl$_2$ solution was transferred to a dropping funnel and added dropwise to the 9(10)-mercaptostearic acid solution. After all of the sulfur monochloride had been added, the reaction mixture was refluxed for 2 hours to drive off the hydrogen chloride. The resultant clear reddish-brown solution was stirred overnight after which the solvent was removed under reduced pressure (about 20 mm. Hg line vacuum) with gentle warming by an infrared lamp. The bis[octadecanoic acid 9(10)-yl]tetrasulfide was recovered as a dark brown liquid.

EXAMPLE 3

The tetrasulfide products of Examples 1 and 2 were each dissolved at an addition level of 5% in white, heavy, domestic, paraffinic mineral oil having a Saybolt viscosity of 335/350 and a weld point of 130. Control compositions were prepared which consisted of the mineral oil alone, mineral oil containing 5% sulfurized sperm whale oil (7.5% S) and 5% sulfurized sperm whale oil (10% S). All of the above lubricant compositions were tested for extreme pressure properties according to ASTM Method D 2596 (reported as weld point, kg.) and wear preventative characteristics according to ASTM Method D 2266-67 (reported as wear scars, mm.). The results appear in the Table below.

Table

| Additive[1] | % Sulfur[2] Calc. | % Sulfur[2] Found | Weld point (kg.) | Wear scars (mm.) |
|---|---|---|---|---|
| Example 1 | 20.2 | 19.3 | 240 | 0.80 |

Table-continued

| Additive[1] | % Sulfur[2] Calc. | % Sulfur[2] Found | Weld point (kg.) | Wear scars (mm.) |
|---|---|---|---|---|
| Example 2 | 18.4 | 8.0 | 580 | 0.74 |
| Sulfurized sperm oil | — | 7.5 | 190 | 0.580 |
| Sulfurized sperm oil | — | 10.0 | 220 | 0.558 |
| Mineral oil | 0 | 0 | 130 | 0.710 |

[1]5% solution in mineral oil.
[2]Percent sulfur in additive.

It is understood that the foregoing detailed description is given merely by way of illustration and that modification and variations may be made therein without departing from the spirit and scope of the invention.

We claim:

1. Tetrasulfide compounds having the structural formula:

wherein $R^1$ and $R^2$ are each independently selected from the following substituent groups:

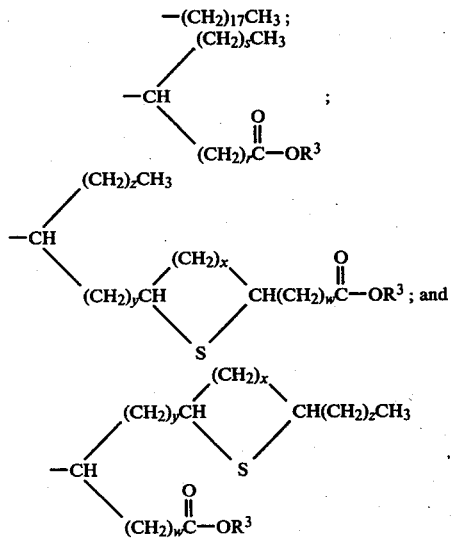

wherein $R^1$ and $R^2$ are not both —$(CH_2)_{17}CH_3$;
wherein r and s are each in the range of 4–10 with the proviso that $r+s=15$;
wherein w and y are each in the range of 1–8, x is 2 or 3, and z is in the range of 0–8, with the proviso that $w+x+y+z=13$; and
wherein $R^3$ is hydrogen; $C_1$–$C_5$ straight or branched alkyl; or

wherein $R^4$ and $R^5$ are each independently selected from the acyl radicals or $C_{16}$–$C_{18}$ saturated and unsaturated fatty acids, and from the acyl radicals of the mercapto, thiolan, and thiane derivatives of $C_{18}$ unsaturated fatty acids.

2. The tetrasulfide compounds as described in claim 1 wherein $R^1$ and $R^2$ both correspond to structural formula II and $R^3$ is hydrogen or methyl.

3. The tetrasulfide compounds as described in claim 2 wherein $R^3$ is hydrogen.

4. The tetrasulfide compounds as described in claim 1 wherein $R^1$ and $R^2$ are each independently selected from structural formulas III and IV, wherein w is 6–8, x is 2, y is 2 or 3, and z is 1 or 2, and wherein $R^3$ is hydrogen or methyl.

5. A lubricating composition comprising a base lubricating oil and an effective amount of an extreme pressure additive, said additive comprising a tetrasulfide compound having the structural formula:

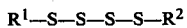

wherein $R^1$ and $R^2$ are each independently selected from the following substituent groups:

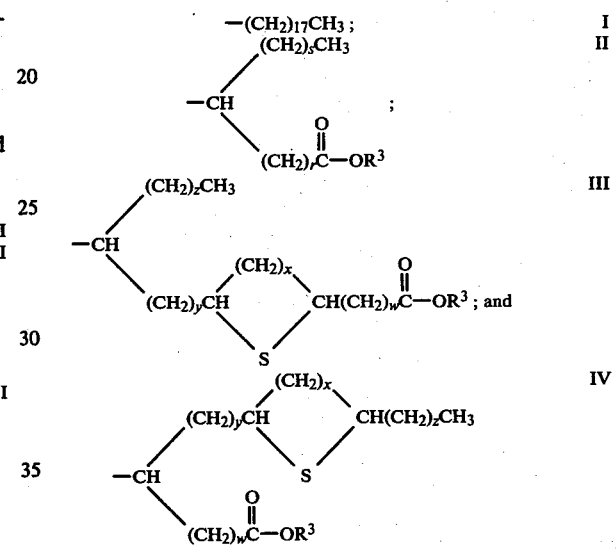

wherein $R^1$ and $R^2$ are not both —$(CH_2)_{17}CH_3$;
wherein r and s are each in the range of 4–10 with the proviso that $r+s=15$;
wherein w and y are each in the range of 1–8, x is 2 or 3, and z is in the range of 0–8, with the proviso that $w+x+y+z=13$; and
wherein $R^3$ is hydrogen; $C_1$–$C_5$ straight or branched alkyl; or

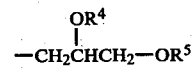

wherein $R^4$ and $R^5$ are each independently selected from the acyl radicals of $C_{16}$–$C_{18}$ saturated and unsaturated fatty acids, and from the acyl radicals of the mercapto, thiolan, and thiane derivatives of $C_{18}$ unsaturated fatty acids.

6. A lubricating composition as described in claim 1 wherein $R^1$ and $R^2$ both correspond to structural formula II and $R^3$ is hydrogen or methyl.

7. A lubricating composition as described in claim 6 wherein $R^3$ is hydrogen.

8. A lubricating composition as described in claim 1 wherein $R^1$ and $R^2$ are each independently selected from structural formulas III and IV, wherein w is 6–8, x is 2, y is 2 or 3, and z is 1 or 2, and wherein $R^3$ is hydrogen or methyl.

* * * * *